(12) United States Patent  (10) Patent No.: US 8,414,557 B2
Istoc et al.  (45) Date of Patent: *Apr. 9, 2013

(54) MODULAR EXTERNAL INFUSION DEVICE

(75) Inventors: Emilian Istoc, Long Beach, CA (US); Himanshu Patel, Northridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/450,293

(22) Filed: Apr. 18, 2012

(65) Prior Publication Data

US 2012/0203196 A1  Aug. 9, 2012

Related U.S. Application Data

(60) Continuation of application No. 13/339,316, filed on Dec. 28, 2011, which is a continuation of application No. 12/881,076, filed on Sep. 13, 2010, now Pat. No. 8,182,462, which is a continuation of application No. 12/286,907, filed on Oct. 2, 2008, now Pat. No. 7,815,622, which is a division of application No. 11/225,359, filed on Sep. 13, 2005, now Pat. No. 7,713,240.

(51) Int. Cl.
*A61M 31/00* (2006.01)

(52) U.S. Cl.
USPC .............. 604/504; 604/131; 604/151; 604/65

(58) Field of Classification Search ............ 604/31, 604/65–67, 131, 151, 504
See application file for complete search history.

(56) References Cited

U.S. PATENT DOCUMENTS

| | | | |
|---|---|---|---|
| 4,433,072 | A | 2/1984 | Pusineri et al. |
| 4,494,950 | A | 1/1985 | Fischell |
| 4,562,751 | A | 1/1986 | Nason et al. |
| 4,671,288 | A | 6/1987 | Gough |
| 4,678,408 | A | 7/1987 | Nason et al. |
| 4,685,903 | A | 8/1987 | Cable et al. |
| 4,731,726 | A | 3/1988 | Allen, III |
| 4,781,798 | A | 11/1988 | Gough |
| 4,871,351 | A | 10/1989 | Feingold |

(Continued)

FOREIGN PATENT DOCUMENTS

| | | |
|---|---|---|
| EP | 0 595 474 A2 | 4/1994 |
| EP | 0 846 440 A2 | 6/1998 |

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Laura Bouchelle
(74) *Attorney, Agent, or Firm* — Pillsbury Winthrop Shaw Pittman LLP

(57) ABSTRACT

A modular external infusion device that controls the rate a fluid is infused into an individual's body, which includes a first module and a second module. More particularly, the first module may be a pumping module that delivers a fluid, such as a medication, to a patient while the second module may be a programming module that allows a user to select pump flow commands. The second module is removably attachable to the first module.

30 Claims, 6 Drawing Sheets

U.S. PATENT DOCUMENTS

| | | |
|---|---|---|
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,355,228 A | 10/1994 | Mizuno et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,543,326 A | 8/1996 | Heller et al. |
| 5,569,186 A | 10/1996 | Lord et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,750,926 A | 5/1998 | Schulman et al. |
| 5,779,665 A | 7/1998 | Mastrototaro et al. |
| 5,791,344 A | 8/1998 | Schulman et al. |
| 5,871,465 A | 2/1999 | Vasko |
| 5,904,708 A | 5/1999 | Goedeke |
| 5,917,346 A | 6/1999 | Gord et al. |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,259,937 B1 | 7/2001 | Schulman et al. |
| 6,329,161 B1 | 12/2001 | Heller et al. |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,554,798 B1 | 4/2003 | Mann et al. |
| 6,558,320 B1 | 5/2003 | Causey, III et al. |
| 6,560,471 B1 | 5/2003 | Heller et al. |
| 6,565,509 B1 | 5/2003 | Plante et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,018,361 B2 | 3/2006 | Gillespie, Jr. et al. |
| 7,109,878 B2 | 9/2006 | Mann et al. |
| 7,815,622 B2 | 10/2010 | Istoc et al. |
| 8,182,462 B2 * | 5/2012 | Istoc et al. .................. 604/504 |
| 2001/0044602 A1 | 11/2001 | Angersbach et al. |
| 2002/0082665 A1 | 6/2002 | Haller et al. |
| 2002/0161288 A1 | 10/2002 | Shin et al. |
| 2003/0078560 A1 | 4/2003 | Miller et al. |
| 2003/0088166 A1 | 5/2003 | Say et al. |
| 2003/0152823 A1 | 8/2003 | Heller et al. |
| 2003/0168338 A1 | 9/2003 | Gao et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2004/0225252 A1 | 11/2004 | Gillespie, Jr. et al. |
| 2005/0065464 A1 | 3/2005 | Talbot et al. |
| 2005/0214585 A1 | 9/2005 | Li et al. |

FOREIGN PATENT DOCUMENTS

| | | |
|---|---|---|
| EP | 0 985 420 A2 | 3/2000 |
| EP | 1338295 A1 | 8/2003 |
| JP | H05-347727 | 12/1993 |
| JP | H07-255091 | 10/1995 |
| JP | H08-160534 | 6/1996 |
| JP | 11-19210 | 1/1999 |
| JP | 11019210 A | 1/1999 |
| JP | 11-507250 | 6/1999 |
| JP | 2002-723 | 1/2002 |
| JP | 2002-523149 | 7/2002 |
| JP | 2003-502090 | 1/2003 |
| JP | 2003-520091 | 7/2003 |
| JP | 2004-775 | 1/2004 |
| JP | 2004000775 A | 1/2004 |
| JP | 2004-515280 | 5/2004 |
| WO | WO 96/37246 A1 | 11/1996 |
| WO | WO 98/03215 | 1/1998 |
| WO | WO 00/10628 | 3/2000 |
| WO | WO 00/29047 A1 | 5/2000 |
| WO | WO 01/52727 A1 | 7/2001 |
| WO | WO 02/45798 A2 | 6/2002 |
| WO | WO 02/058537 A2 | 8/2002 |
| WO | WO 02/066101 A2 | 8/2002 |
| WO | WO 03/105931 A1 | 12/2003 |

OTHER PUBLICATIONS

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'dimethylferrocene mediated glucose biosensor,"Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v.1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.

Nakamato et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Using Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected by Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta., 1989, pp. 137-142, vol. 218.

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-3179, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n.10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and in Vitro Studies of a Needle-Type Glucose Sensor for Subcutaneous Monitoring," Anal. Chem., 1991, pp. 1692-1696, vol. 63.

PCT International Search Report, Feb. 6, 2007 (PCT/US2006/035035) (5-pages).

* cited by examiner

MODULAR EXTERNAL INFUSION DEVICE

RELATED APPLICATION DATA

This is a continuation of U.S. patent application Ser. No. 13/339,316, filed Dec. 28, 2011, which is a continuation of U.S. patent application Ser. No. 12/881,076, filed Sep. 13, 2010, now U.S. Pat. No. 8,182,462, which is a continuation of U.S. patent application Ser. No. 12/286,907, filed Oct. 2, 2008, now U.S. Pat. No. 7,815,622, which is a divisional of U.S. patent application Ser. No. 11/225,359, filed Sep. 13, 2005, now U.S. Pat. No. 7,713,240, and is related to U.S. patent application Ser. No. 12/727,170, filed Mar. 18, 2010, now U.S. Pat. No. 8,152,764, all of which are incorporated herein by reference.

BACKGROUND OF THE INVENTION

1. Field of the Invention

Embodiments of this invention are related generally to an external infusion device, and more particularly, to a modular external infusion device that controls the rate a fluid is infused into an individual's body.

2. Description of Related Art

Infusion devices and systems are relatively well known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter or infusion set.

Infusion devices and systems generally include a display and an input device. In infusion devices known in the art, the display and input device are part of the pump housing. Thus, the entire infusion device, including any input and output devices, is composed in a unitary housing. A drawback to these infusion devices is that they may be too bulky and/or heavy to conveniently wear.

There are a number of infusion devices developed to alleviate the problems associated with weight and bulkiness. Such infusion devices may include a small drive motor connected via a lead screw assembly for motor driven advancement of a reservoir piston to administer the medication to the user. Programmable controls can operate the drive motor continuously or at periodic intervals to obtain a closely controlled and accurate delivery of the medication over an extended period of time. These infusion devices are used to administer insulin and other medications, with exemplary pump constructions being shown and described in U.S. Pat. Nos. 4,562,751; 4,678,408; 4,685,903; 5,080,653; 5,097,122, and 6,551,276, which are incorporated by reference herein.

Infusion devices of the general type described above have provided significant advantages and benefits with respect to accurate delivery of medication or other fluids over an extended period of time. The infusion device can be designed to be extremely compact as well as water resistant, and may thus be adapted to be carried by the user, for example, by means of a belt, clip, or the like. As a result, important medication can be delivered to the user with precision and in an automated manner, without significant restriction on the user's mobility or life style, including in some cases, the ability to participate in water sports. However, there remains a need in the art for an infusion device, with the capabilities of the above-described infusion devices but, that is also capable of being even more compact.

BRIEF SUMMARY OF THE INVENTION

In accordance with embodiments of the invention, a modular external infusion device is provided that controls the rate a fluid is infused into an individual's body. An embodiment of the present invention includes a first module and a second module. The first module may be a pumping module that delivers a fluid, such as a medication, to a patient.

The second module is removably attachable to the first module. In one embodiment, the second module may be attached by sliding onto the first module. Alternatively, the second module may be attached to the first module by parts, such as sliding parts that mate. In another embodiment, the second module may be attached to the first module by snapping parts that mate. Other alternatives, such as screwing components, hook and loop fasteners (e.g., Velcro™), adhesives, and the like, may also be used.

In further embodiments, the second module is a programming module that allows a user to select pump flow commands. In these embodiments, the second module contains a user interface and controls the first module. Where the first module is a pumping module, the second module preferably controls the pumping of the first module. The control by the second module of the first module does not necessarily need to be constant or continuous. For example, in a preferred embodiment, the second module inputs a pumping schedule to the first module. The first module will then pump based on the inputted schedule without any further inputs from the second module. In this way, the first module may continue its pumping schedule even when disconnected from the second module.

The pumping of the first module may be driven by any desired drive mechanism. Example drive mechanisms include, but are not limited to, gas, drive syringe, and electrolytic.

In particular embodiments, the second module has a display with one or more input devices, such as for example, buttons or keys. The display may be a touch screen display that can be used in conjunction with the input devices. The touch screen may be used in conjunction with, or as an alternative to, the buttons or keys. The display may be adapted to display various icons on the touch screen display, including multi-national icons that can be interpreted by users regardless of language. Display settings may be customizable, including, but not limited to, the background, sounds, fonts, and wallpaper. Different display features may be provided by the module and/or may be downloaded from a computer.

The second module may communicate with the first module by any suitable method. For example, the communication may be a direct connection, as by electrical contacts or wire. Alternatively, it may be a wireless method, such as radio frequency (RF) or magnetic induction.

In a preferred embodiment where the second module controls the pumping of the first module, the first module contains a pumping mechanism. The pumping mechanism can be any mechanism known in the art and suitable for pumping fluid. The first module can be used with or without the second module. It preferably can operate semi-independently from the second module while keeping in contact with it. It is preferably compact so that it can be worn under clothing if desired.

The second module may be used in conjunction with the first module, for example, to control the pumping features. It may also be used for stand-alone applications, such as sensing an analyte level of the patient. The second module may have a sensor interface, an analyte meter, or both. The analyte may be, for example, blood glucose. The sensor may be, for example, a glucose sensor. The blood glucose meter may be housed in the second module. The second module may have a receiver, in addition to or instead of the blood glucose meter, to receive information transmitted from a separate blood glucose meter. The second module may be configured to communicate with a blood glucose meter and/or a glucose sensor. The communication between the second module and the blood glucose meter and/or glucose sensor may be wireless or wired.

In particular embodiments of the invention, the first module and/or the second module may have one or more alarms. Alarms may be audible, tactile, and/or visual. Alarms may indicate low or high blood glucose levels or infusion device problems, such as for example, blockages or overdelivery of fluids in the pump. In certain embodiments, the alarm may sound whenever blood glucose levels go beyond a programmed or allowed range. The second module may also include alarm(s) where the first module does not include any. The second module and/or the first module may include a speaker, which may be configured to output alarms and other sounds. The sounds may sound like a buzzer or another noise. The sounds may be words. For example, if the user's blood glucose is high, an alarm may be a sound that states, "Your blood glucose is high."

One or both of the second module and the first module may communicate to a personal computer. The communication may be wired or wireless. For example, the modules may communicate with the computer when inserted into a docking station or when connected by a wire to the computer. The communication may be wireless, such as RF, Bluetooth, or any other wireless method.

In further embodiments, a computer software program may be used that is essentially a virtual second module. The same commands and controls that exist in the second module may exist in the computer program. The second module may be synched with the computer program on the computer, so that changes made on the computer are indicated in the second module, and vice versa.

The first module may have a button or switch or other input device to stop the pump in an emergency. To avoid accidental activation of the emergency stop, there may be a safety feature implemented. For example, if the emergency stop is a button, the stop might not be activated until the button is pressed for a continuous period of time, for example two seconds. In an alternative, there may be two buttons that both need to be pressed at the same time.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE INVENTION

Figure 1:
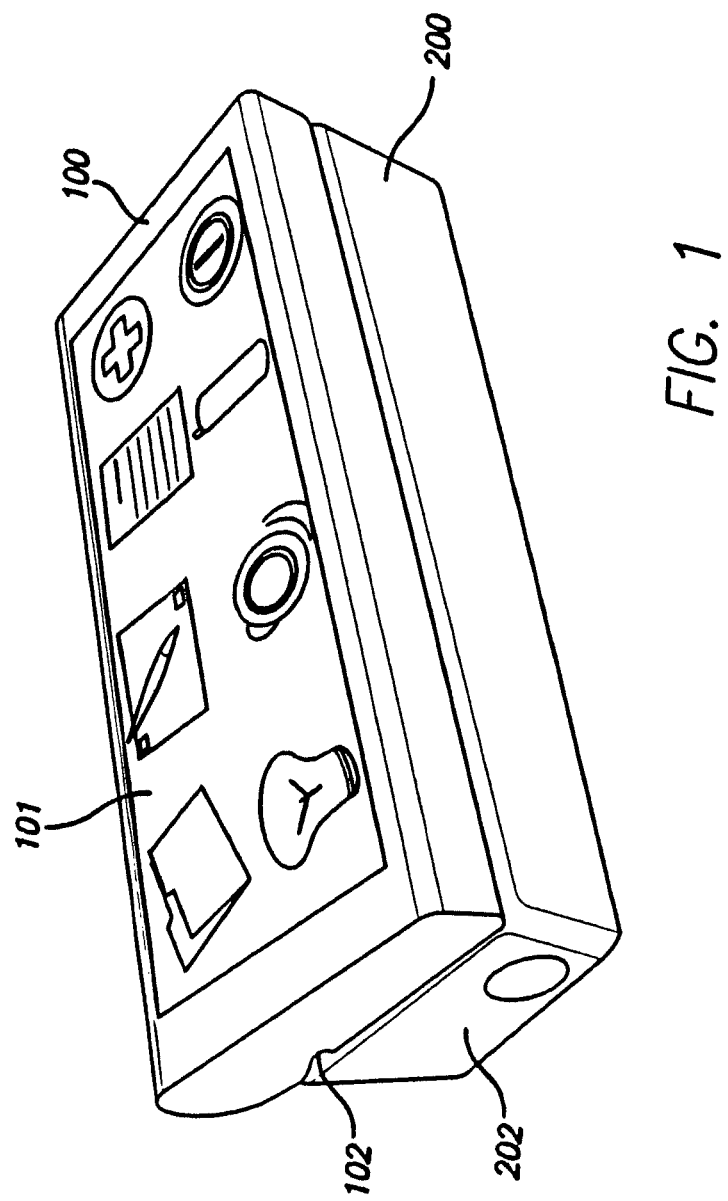
FIG. 1 is a perspective view of a modular external infusion device in accordance with an embodiment of the present invention.

In the following description, reference is made to the accompanying drawings which form a part hereof and which illustrate several embodiments of the present inventions. It is understood that other embodiments may be utilized and structural and operational changes may be made without departing from the scope of the present inventions.

As shown in the drawings for the purposes of illustration, the invention is embodied in a modular external infusion device. In preferred embodiments, the modular external infusion device includes a first module and a second module. In further preferred embodiments, the first module is a pumping module, which is adapted to deliver a fluid to a patient. The fluid may be a medication, such as insulin.

In preferred embodiments, the second module contains a user interface and controls the first module. Where the first module is a pumping module, the second module may be a programming module and preferably controls the pumping of the first module. The control by the second module of the first module is not necessarily a continuous control. For example, in a preferred embodiment, the second module communicates a pumping schedule to a first module. The first module will then pump based on the inputted schedule without any further communicates from the second module. The inputted schedule may be stored in a memory, such as a flash memory. In this way, the first module may continue its pumping schedule even when disconnected from the second module.

The pumping of the first module may be driven by any desired drive mechanism. Example drive mechanisms include, but are not limited to, gas, drive syringe, and electrolytic.

As shown in FIG. 1, the modular external infusion device according to embodiments of the invention includes a second module 100 and a first module 200. Although the second module 100 is shown as resting on top of the first module 200, the second module 100 could be on the bottom, the two modules could rest side-to-side, or they could be configured in any other way that allows the two modules to be placed together. The first module 200 contains the pumping mechanism. The pumping mechanism can be any one of the suitable pumping mechanisms in the art. For example, the pumping mechanism may include a piston-type drive system as described in U.S. Pat. No. 6,248,093, which is herein incorporated by reference. Further exemplary infusion device constructions are shown and described in U.S. Pat. Nos. 4,562,751; 4,678,408; 4,685,903; 5,080,653; and 5,097,122. In certain embodiments, the second module controls the pumping of the first module. The second module may also include a blood glucose meter and/or could interface with any desired, available blood glucose meter. It may also be configured to mate with or slide over a blood glucose meter.

Figure 2:
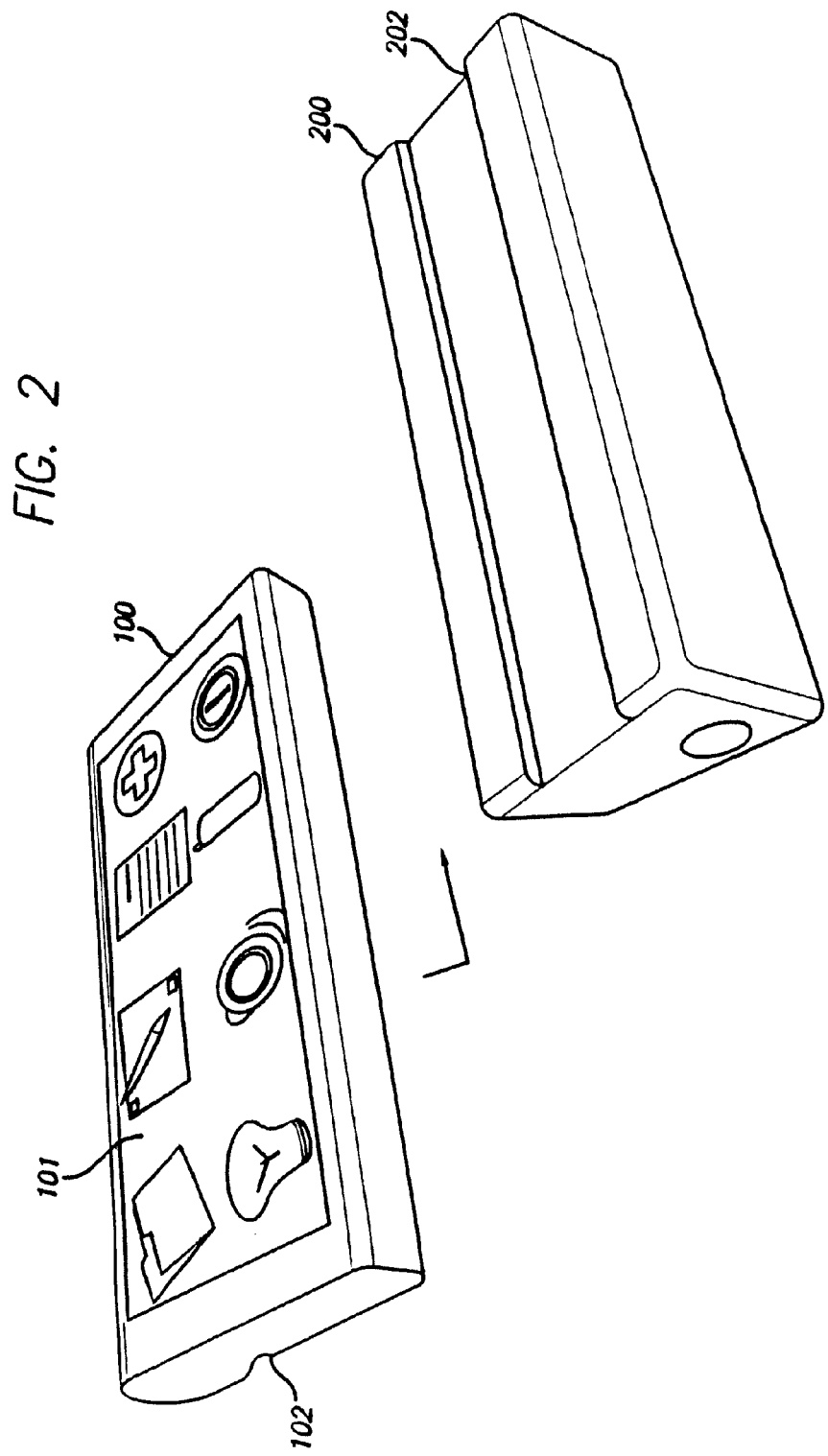
FIG. 2 is a perspective view of a modular external infusion device with arrows indicating the manner in which a first module and a second module fit together in accordance with an embodiment of the present invention.

As shown in FIG. 2, in certain embodiments, the second module 100 is removably attachable to the first module 200. For example, the second module 100 may be attached to the first module 200 by sliding parts 102, 202 that mate. In another embodiment, the second module may be attached to the first module by snapping parts that mate. Other alternatives, such as screwing components, hook and loop fasteners (Velcro™), adhesives, and the like, may also be used. In this manner, the second module may be easily removed and attached from the first module without interrupting or discontinuing the pumping schedules. Consequently, the user is given an option to wear the first module without the second module, making the infusion device even lighter and less bulky.

Although the second module and the first module are shown as being block-shaped, they could be shaped in a number of different ways. For example, the second module could be shaped in any way that is suitable to interface with the first module and to allow the user to view the display and input commands. The first module could be shaped in a way that is able to hold a desired amount of medication. Example shapes include, but are not limited to, a pen shape, a flat shape, and a round shape. A hospital pump may also be used as the first module.

As shown in FIGS. 1 and 2, the second module 100 has a display 101. The display acts as part of a user interface. The display may be, for example, an organic light emitting diode (OLED) display, a light emitting diode (LED) display, and a liquid crystal display (LCD). In an embodiment with the OLED display, the display is self luminous and consequently does not require an additional backlight to illuminate the display. The display may be a touch screen display that allows the user to touch the screen to input data and/or commands into the second module.

In addition to, or instead of (in the case of a touch screen display) the display, the second module may have one or more input devices, such as buttons or keys for example. In further embodiments, alternative input devices such as joysticks, touch pads, track balls, a keyboard, and/or a microphone for voice commands may also be used. The second module may contain a camera to store pictures that may be displayed on the second module display. The display may be adapted to display one or more icons. The user may use the input device(s) to select icons and/or, in the case of a touch screen display, the user may select the icons by touching the display at the locations of the icons he wishes to select. There can be any number of kinds of icons, for example, icons could include basal icons, bolus icons, sensor trend icons, food index and/or nutritional index icons, data transfer icons, power icons, settings icons, log book icons, alarm icons, exercise icons, sleep icons, eat icons, favorites, icons, most recent use icons, and so forth. The icons presented on the user interface may be customizable to represent a particular thing that the user, a patient, doctor, parent, or other user, may want to do. For example, a doctor may wish to include an icon for a temporary basal rate that a patient commonly uses. In that case, the patient could activate the temporary basal rate icon to start that particular temporary basal rate or to go directly to a temporary basal rate screen.

It is noted that some users can be expected to have somewhat diminished visual and tactile abilities due to the complications from diabetes or other conditions. Thus, the display and buttons or other input devices may be configured and adapted to the needs of a user with diminished visual and tactile abilities. In alternative embodiments, the second module (and/or the first module) may communicate to the user by audio signals, such as beeps, speech or the like.

Other display settings may be customizable, including, but not limited to, the background, sounds, fonts, and wallpaper. There may be a children's mode, with limited features available so that a child cannot dispense too much medication at once. Different display features may be included in the module and/or may be downloaded from a computer. The second module may have a memory with which to store customized settings or pump control. The memory may be of any type that is known in the art, such as a volatile or non-volatile memory. Both a volatile and non-volatile memory may be used, which can speed up operation of the pump. As an example, non-volatile memories that could be used in the invention include flash memories, thumb drives and/or memory sticks such as USB thumb drives, removable hard drives, and optical drives.

The second module preferably has a real time operating system (RTOS). The user interface may be a multi-national icon driven one, with or without text. A multi-national icon driven interface may reduce development, testing, and validation time while also decreasing the learning curve on the part of the user. Alternatively, the user interface may be text based and may or may not incorporate scrolling to allow the user to scroll through text.

Figure 3:
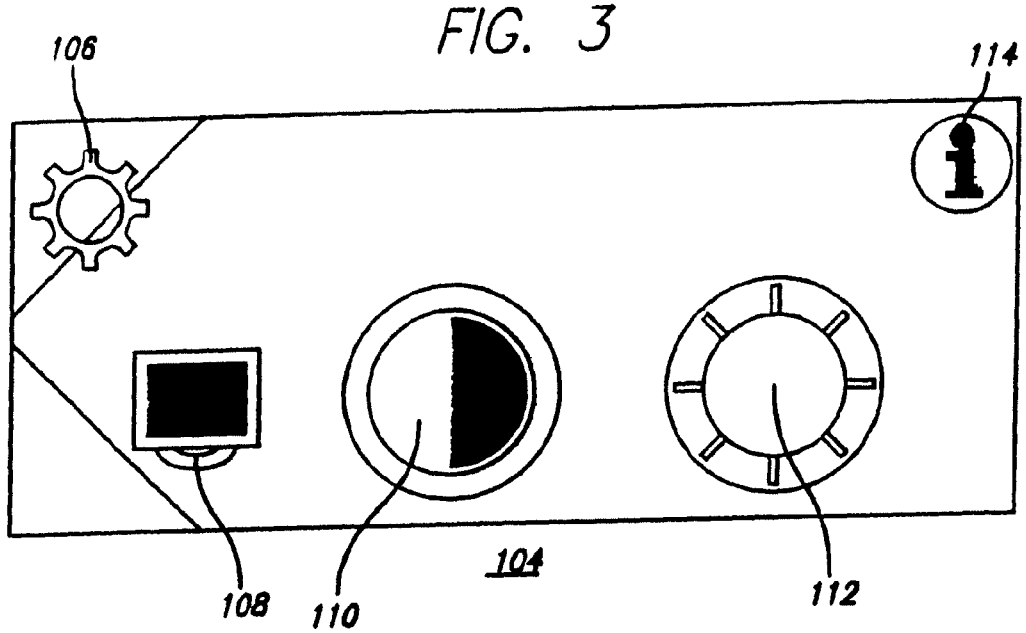
FIG. 3 is a top view of a second module displaying a Notes Menu in accordance with an embodiment of the present invention.
Figure 4:
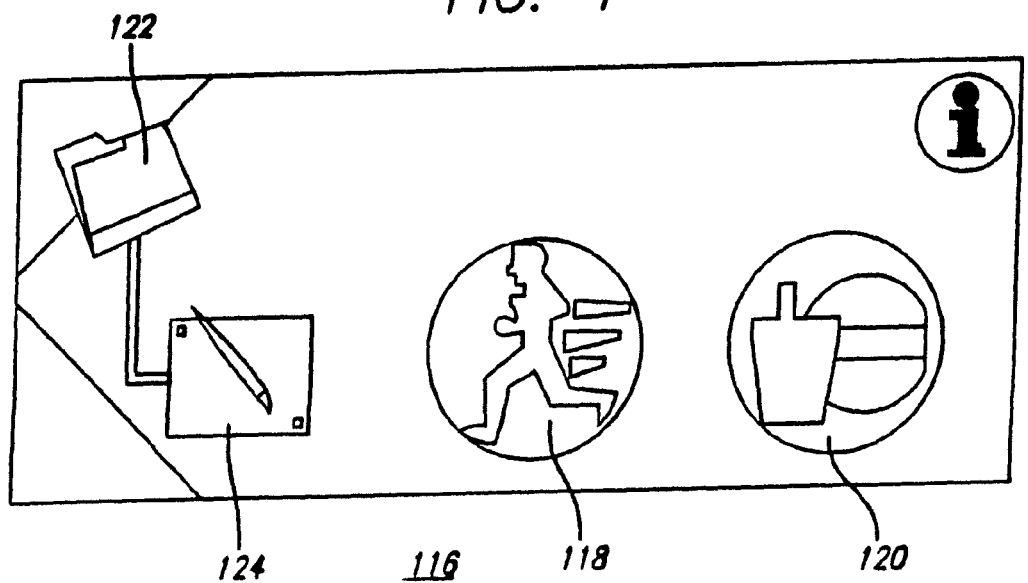
FIG. 4 is a top view of a second module displaying a Screen Menu in accordance with an embodiment of the present invention.
Figure 5:
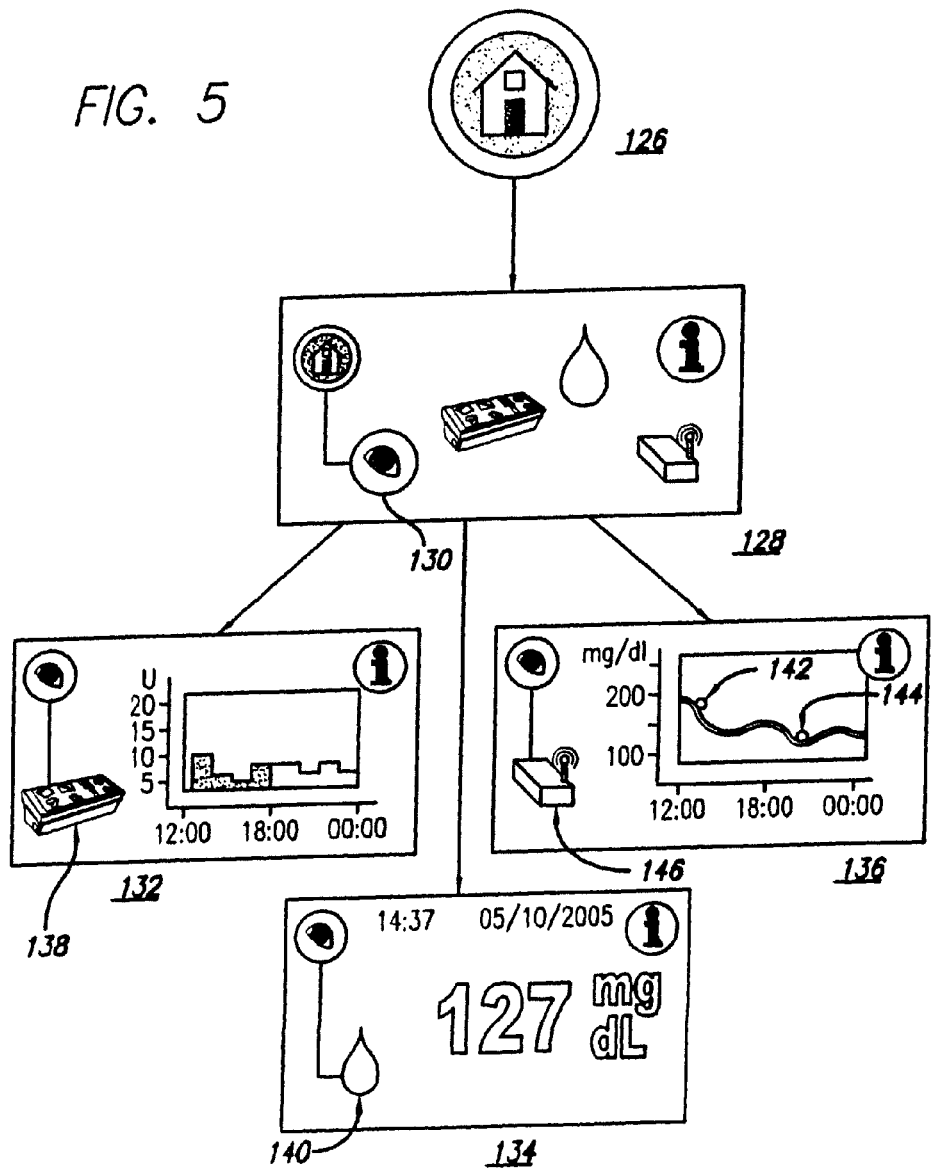
FIG. 5 is a top view of a second module displaying a View Menu as a root menu for three submenus in accordance with an embodiment of the present invention.

Shown in FIGS. 3-5 are a number of possible screens that may be used on the display for a user interface in embodiments of the invention. Each of these screens may display a specific user menu with icons that the user may use to select different options for programming insulin delivery and/or selecting different infusion device features. The menus may all be interrelated so that a user may navigate and access each menu from the other menus. Each menu icon may be categorized as a "root menu" or an "active menu." A root menu represents the previous menu that the current menu derives from, or the last menu visited by the user. This may be shown as the icon located at the upper left corner. A white pipe line may be used to link the root menu to the current menu, shown as an icon located at the bottom left corner. An active menu represents the present menu selected, from which the user may choose to continue accessing other submenus by selecting the icons displayed on the active menu screen.

In FIG. 3, one embodiment of such a user menu is shown. The Screen Menu 104 allows a user to adjust the settings of the display of the second module. The root menu is depicted as a settings wheel 106 and the active menu is depicted as a computer monitor 108. Other icons shown include the standard contrast icon 110 and brightness icon 112. In the upper right hand corner, the information icon 114 is shown. The user may select the information icon 114 to query for more information about the current menu items displayed. In one embodiment, the information icon is displayed on all of the menus.

An embodiment of another menu is shown in FIG. 4, illustrating a Notes Menu 116. The Notes Menu 116 may include several icons regarding exercise 118 and meal events 120, which the user may use to enter these events and factor them into the pumping schedules. In the embodiment, the root menu is depicted as a folder 122 and the active menu is depicted as a desktop with a pen 124. The menu may also allow the user to take notes and store the notes into either the second module or the first module for future reference.

FIG. 5 further illustrates menus that may be included in embodiments of the invention. The menus may be interrelated so that each menu is accessible from other menus. For example, in FIG. 5, a base menu is depicted by a house icon 126, and from that menu, three other menus may be accessed through the View menu (the active menu) 128 represented by the eye icon 130. The three submenus may include a Pump Graph Menu 132, a Blood Glucose Reading Menu 134, and a Sensor Graph Menu 136. The Pump Graph Menu 132 shows the user a graph of the insulin delivery over a selected time. The active menu is indicated by the pump icon 138. The Blood Glucose Reading Menu 134 shows the current blood glucose reading that is either determined by a blood glucose meter included in the second module, or received or transmitted from a separate blood glucose meter. The active menu is indicated by the blood drop icon 140. The Sensor Graph Menu 136 shows the user a graph of the sensor readings over time. The menu may also show the calibration points 142, 144 for the sensor on the graph. The sensor readings may be received via RF. The active menu is indicated by the RF receiver icon 146.

The various menus allow the user to input information that is communicated from the second module to the first module. In a preferred embodiment, the pumping mechanism of the first module is controlled by the second module according to the information supplied by the user. The second module may communicate to the first module through RF or magnetic induction. The second module may communicate with the first module through wired or wireless connections, and other methods. For example, the communication may be a direct connection, as by electrical contacts or wire. Other types of communication might include, for example, an RS232 connection, a USB connection, or a wired Ethernet connection, Bluetooth, ZigBee, 802.11 protocol, wireless local area network (LAN) or a wireless Ethernet connection.

Figure 6:
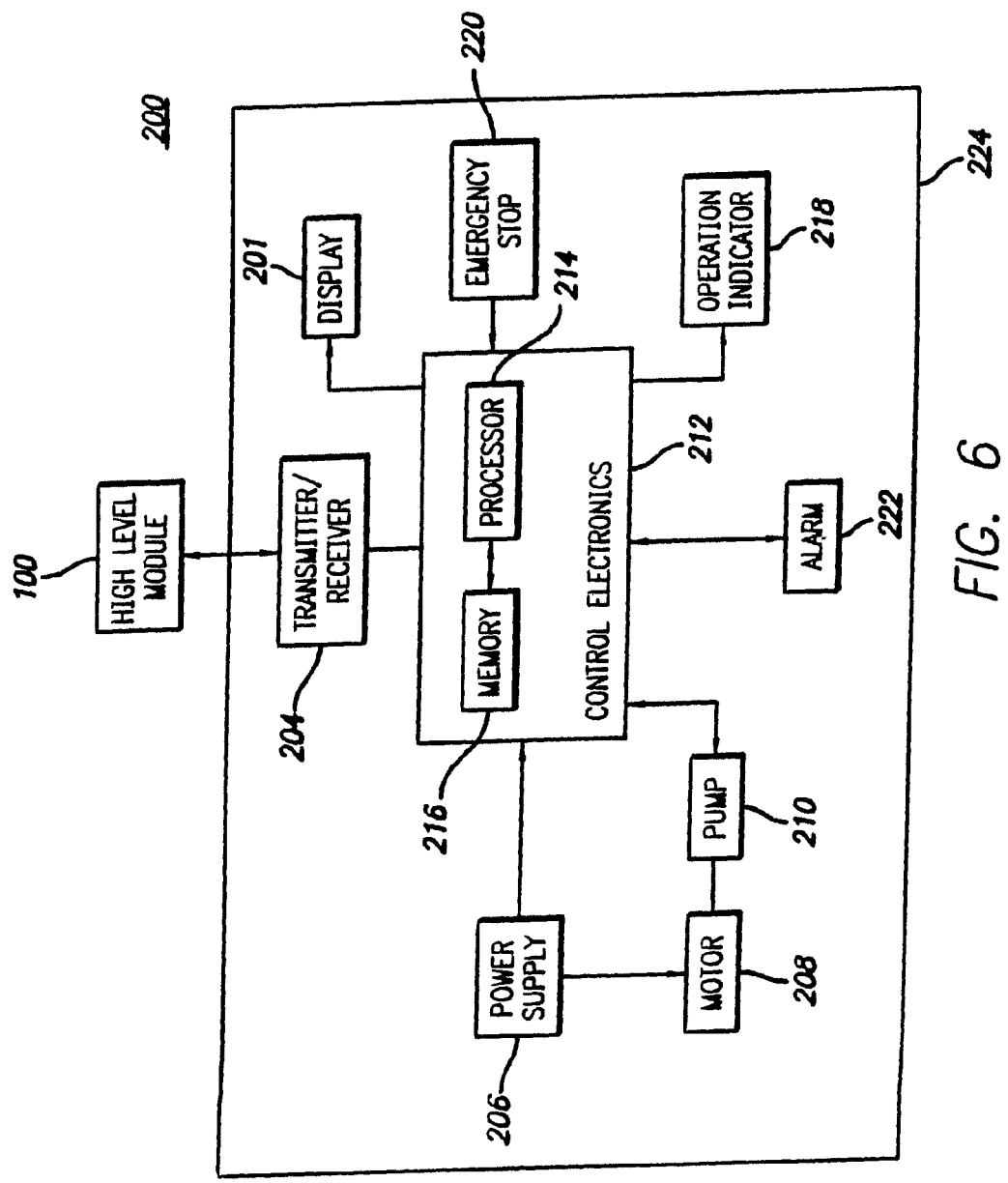
FIG. 6 is a simplified block diagram of a first module in accordance with an embodiment of the present invention.

In one embodiment, as shown in FIG. 6, the first module 200 is a pumping module that includes a pump 210, a motor 208, and an alarm 222, which are all comprised in or on a first module case 224. A display 201 may be located on the module case 224. The first module 200 may include a power supply 206, discussed in more detail below. The first module may further include control electronics 212 having a memory 216 to store pumping programs and/or commands and a processor 214 to process the commands to control the pumping of the module. The first module 200 may include an operation indicator 218, which may be a simple light or other type of visual signal to indicate that the pump is operating. Alternatively, the operation indicator may be on the display 201, such as an LED display. The alarm 222 may be a tactile alarm, such as a vibrating alarm, an audible alarm and/or a visual alarm. It is preferred that the first module have at least minimum safety features, such as the alarm, that can indicate malfunctions.

The first module may receive instructions sent by the second module transmitter through its receiver 204. In some embodiments, both a transmitter and receiver may be included in the first module. The combined transmitter/transceiver configuration is also known as a transceiver. In this way, the first module may receive instructions from the second module as well as send back signals to the second module to better maintain fluid delivery. Likewise, the second module may include a transceiver so that both the first and second modules may send and receive signals from one another.

The first module may have a button or switch or other input device to stop the pump in an emergency 220. To avoid the emergency stop 220 being activated accidentally, there may be a safety feature implemented. For example, if the emergency stop is a button, the stop might not be activated until the button is pressed for a continuous period of time, for example two seconds. There may be two buttons that both need to be pressed at the same time. In further embodiments, the first module may also have general input devices, like buttons or keys, to input instructions or program fluid delivery.

Although the first module described in this embodiment is a pumping module, it is envisioned that a number of different kinds of first modules could be used with the second module. For example, the second module could work with a first module that is a continuous glucose sensor and/or a blood glucose meter.

Figure 7:
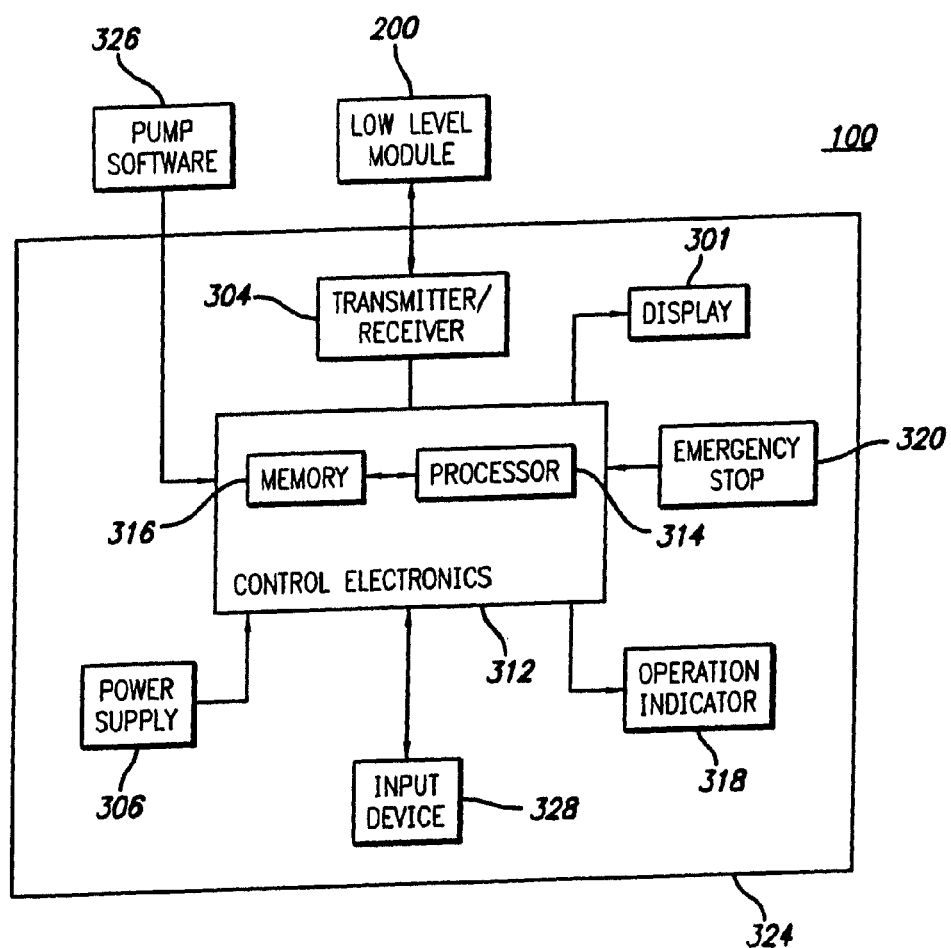
FIG. 7 is a simplified block diagram of a second module in accordance with an embodiment of the present invention.

In one embodiment, as shown in FIG. 7, the second module 100 includes a processor 314 in communication with a display 301. The display 301 may be located on the module case 324. The processor 314 is also in communication with any input device 328, such as keys or buttons. The second module 100 includes a memory 316, in communication with the processor 314, for storing information input from the input device(s) 328 and for output on the display 301, where the processor 314 and memory 316 are part of the control electronics 312. In addition, the memory 316 is adapted to store any programs loaded as part of the pump software 326. The first module preferably has software similar to that in the second module, but without the same user interface.

The second module may send instructions to the first module through its transmitter 304. In some embodiments, both a transmitter and receiver may be included in the second module. The combined transmitter/transceiver configuration is also known as a transceiver. In this way, the second module may both send instructions to and receive instructions from the first module to better maintain fluid delivery. Likewise, the first module may include a transceiver so that both the second and first modules may send and receive signals from one another.

The first module, with its pumping module, preferably has a very limited user interface for operational and/or basal indication and emergency bolus. The second module 100 may further include a power supply 306, discussed in more detail below. The second module 100 may also include an operation indicator 318, which may be a simple light or other type of visual signal to indicate that the second module 100 is operating. It may additionally include a first module operation indicator that indicates whether the first module 200 is operating. The second module 100 may include emergency stops 320 similar to those that may be included in the first module 200.

The second module and the first module preferably each have their own power supply, although it is possible for there to be a power supply in the first module alone, so that the second module is only connected to a power supply when it is electrically connected to the first module. Each power supply may be rechargeable or disposable. Where the power supply is rechargeable, it may be a rechargeable battery. If the second module has a rechargeable battery, the second power supply may recharge when the second module connects to the first module and/or when the second module is connected to another power supply. For example, the power supply could recharge when the second module is docked in a docking station. The second module may be electrically connected to a power outlet for charging the power supply. The second module could also be connected to a portable battery charger for charging the power supply. Additionally, the power supply could be a kinetically rechargeable battery.

The first module, like the second module, may also have a rechargeable power supply. If the first module has a rechargeable battery, the first power supply may recharge when the first module connects to the second module and/or when the second module is connected to another power supply. A battery recharger may be adapted to recharge one module at a time or both of the second module and the first module at the same time. A battery recharger could also be adapted to charge more than modules, for example for systems that include two first modules. The power supply for either module may be a removable battery that can be recharged separately from the modules. Additionally, it is possible that the first module may be manufactured and sold cheaply enough that the entire module could be disposable at the end of a non-rechargeable battery life. In this case, the battery may be sealed inside the module for better water resistance. Furthermore, the second module and/or the first module themselves may be water resistant. They also may be waterproof. Alternatively, the second and first modules may be manufactured so that the compatibility to operate as an entire module is not limited to a specific counterpart. In this manner, if and when the second module or the first module breaks or is too worn to continue use, a new second or first module may be purchased and be compatible with the remaining counterpart.

A power indicator may be included on the display of the second module and/or the first module so that the user can conveniently check the level of power. The indicator may provide a warning to the user as to when the power supply needs to be recharged or replaced. For example, the intensity of the indicator may correlate with the power level. In addition, a warning indicator may notify the user that the power supply is very low or about to run out by blinking.

In embodiments where the first module is a pump module and is disposable after a period of time, the first module may be pre-filled with the fluid for infusing and intended for a single infusion of fluid. Once all of the fluid has been infused, the first module may be disposed. For example, if the first module holds three days worth of fluid, it would be disposable after three days of use. The amount of fluid included could be equal to the average amount that would be used during the average lifetime of the included battery. Alternatively, more fluid or less fluid could be included so that the battery would likely run out first or so that the fluid would likely run out first. In still other embodiments, the first module may be refillable as to the fluid, but include a non-rechargeable battery that is sealed within the housing. In that case, the first module could be disposable at the end of the battery life. The life of the first module would generally depend on the type of battery used.

The modules may include a number of ways to increase battery life. For example, one or more module could include solar cells to increase the light of the displays and to increase power. In further embodiments, the display may be configured to turn off after a certain amount of time, which may be preset or set by the user. Alternatively, the display may remain on at all times. It may be an option selectable by the user for the display to either remain on at all times or to turn off after a certain amount of time. The entire second module could also be configured to turn off after a certain amount of time to save power. Where the second module inputs a schedule into the first module and is not needed until the next input from the user, it is not necessary for the second module to remain on at all times.

The second module may be used in conjunction with the first module, for example to control the pumping features, or it may also be used for stand-alone applications, such as sensing an analyte level of the patient. The second module may have a sensor interface, an analyte meter, or both. The analyte may be, for example, blood glucose. And the sensor may be, for example, a continuous glucose sensor. Example glucose sensors are described in U.S. Pat. Nos. 5,390,671; 5,391,250; 5,482,473; and 5,586,553, and U.S. application Ser. No. 10/273,767 (published as U.S. Patent Publication No. 2004/0074785 A1, on Apr. 22, 2004), which are herein incorporated by reference. While the blood glucose meter may be housed in the second module, it is also possible that the second module has a receiver, in addition or instead of the blood glucose meter, to receive information transmitted from a separate blood glucose meter. In further embodiments, the first module may be a sensing device or a blood glucose meter. In still further embodiments, the second module may be adapted to interface with two or more first modules. For example, in one embodiment, a blood glucose meter, by itself or including a continuous glucose sensor, is adapted to be a second first module. The modules may stack upon each other, like a sandwich, so that one of the first modules is sandwiched between the other first module and the second module. Alternatively, the modules may be worn separately or side-to-side from each other.

In particular embodiments of the invention the first module has one or more alarms. The second module may also have one or more alarms. Alarms may be audible, tactile, and/or visual. Alarms may indicate low or high blood glucose levels, pumping problems like blockages or overdelivery of fluids, lack of communication between devices, or power failure, for example. In embodiments, the alarm may sound whenever blood glucose levels go beyond a programmed or allowed range. The range may be selected and inputted manually by a user or the range may be calculated based off of a set of governing parameters. The second module may include a speaker, which may be configured to output alarms or other sounds. The sounds may sound like a buzzer or another noise. They may be words. For example, if the user's blood glucose is high, an alarm may sound that says, "your blood glucose is high."

The first module can be used with or without the second module. It is preferably compact so that it can be worn under clothing if desired. It preferably can operate semi-independently from the second module while keeping in contact with it. The first module preferably has a minimal user interface. In one embodiment, it may only have a power switch or on/off button. Where the first module is a pumping module, the first module may instead include an emergency stop button or switch in case the pump alarms. In further embodiments, the first module may include a simple display, such as an LED display, and/or one or more buttons. For example, where the first module is a pumping module, the display may display the pumping rate of the module and the user may use one or more buttons or keys to change the pump rate. In further embodiments, the pumping module may be adapted to display several characteristics of the pumping program, which the user could scroll or select through using one or more buttons or keys. In still further embodiments, the display may be more sophisticated, like an LED or OLED, for example, and/or the first module may include additional or different input devices, such as joysticks, touch pads, track balls, a keyboard, and/or a microphone.

The second module and the first module may use any number of communications protocol. One or both of the second module and the first module may communicate to a personal computer. The communication may be wired or wireless. For example, the modules may communicate with the computer when inserted into a docking station or when connected by a wire to the computer. The communication may be wireless, such as RF, Bluetooth, or any other wireless method. Other types of communication might include, for example, an RS232 connection, a USB connection, or a wired Ethernet connection, Bluetooth, ZigBee, 802.11 protocol, wireless local area network (LAN) or a wireless Ethernet connection. The second module and/or the first module may be configured to interact with an analyte sensor. For example, the second module may to communicate with a blood glucose sensor and/or a glucose meter as well. The sensor may be a continuous glucose sensor. The communication between the second module and the blood glucose sensor and/or glucose meter may also be wired or wireless.

The second module and/or the first module may be configured to notify the user if there are communication problems between any of the devices. When strict medication delivery and monitoring is required, for example a closed-loop system, the first module can be programmed to stop dispensing medication when it fails to receive periodic scheduled communication from the second module or a personal computer (PC) or the like. In the alternative, an alarm may sound when the scheduled communication is not received, rather than stopping the medication dispense. This timeout option and duration is programmable and may also be included in the delivery schedule. The notification may be of one or more types, such as an alarm, an icon on the display, or some other type of notification.

The first module may also be configured to communicate with a blood glucose meter or a blood glucose sensor in the case of a virtual second module. The first and/or second module may further be configured to communicate with implantable devices such as an implantable insulin pump or an implantable blood glucose sensor. The first and/or second module may also communicate and transfer user settings, history data, new software or firmware, and configuration information with other first and/or second modules or PCs. This would allow for system replacements and software upgrades. The first and/or second module may also communicate to more than one pump or sensor modules.

The second module may have an on-pump training mode, so that a user may learn how to use the pump interactively, without having to actually dispense medication. In the on-pump training mode, the second module teaches the user to go through the steps that the user would take to perform an action using the second module. The on-pump training mode may be a mode that is only able to be activated when the second module is separated from any first module. Alternatively, the on-pump training mode may be set up so that a user can enter the training mode at any time. For example, if a user is learning to use a temporary basal rate option, the user might want to enter the training mode to get instruction directly from the second module, instead of from a manual. In further embodiments, the on-pump training mode may allow the user to direct the second module to perform the actions taken during the training mode. For example, during a training session in which the user learns to use a temporary basal rate option, the user may select a temporary basal rate and a time period for delivery of the temporary basal rate option. At the end of the training session, the pump may query the user to determine whether the user wants to run a program so that the pump can proceed at a selected temporary basal rate for a selected time period. If the user selects to run the program, the second module sends an instruction to a first pumping module to pump the selected temporary basal rate for the selected time period. If the user selects to not run the program, the second module does not send an instruction to a first pumping module.

In an embodiment where the second module communicates with a glucose sensor and the first module, it is anticipated that a closed-loop system may be employed. In a closed-loop system, the pump interacts with a continuous glucose sensor to mimic the functions of a healthy pancreas. Preferably, the system works with minimal interaction from the patient. An example of a closed loop system is described in U.S. Pat. No. 6,558,351, which is herein incorporated by reference.

Additionally, one or both of the second module and the first module may communicate with other devices, such as a phone or pager system. In further embodiments, the second module and/or the first module may include a Global Positioning System (GPS) device. Alternatively, the second module and/or the first module may interface with a GPS device. The GPS device can be configured to help the user determine his or her location or get directions to another location, like a standard GPS device used in an automobile. The GPS device can also be used to locate a user from a remote location. For example, if a user has a blood glucose emergency, emergency personnel could use the GPS device to find the user. The GPS may be always on, or intermittently, for example able to be turned on by the user, or turned on automatically if a problem exists.

In further embodiments, there is a computer software program that is essentially a virtual second module. The same commands and controls that exist in the second module may exist in the computer program. The second module may be synched with the computer program on the computer, so that changes made on the computer are indicated in the second module, and vice versa. In still further embodiments, the second module may be adapted to interact with a virtual patient software program that allows a patient and/or a doctor to change different parameters and see how it would affect the patient. The virtual patient software program may receive data from the second module to populate the program parameters. An example of a virtual patient software program is described in pending U.S. Patent Application No. 40088-316103, entitled "Virtual Patient Software System for Educating and Treating Individuals with Diabetes," filed Jun. 3, 2005, which is herein incorporated by reference.

Additional software may be used on the computer for keeping records and analysis of patient data, such as tracking medication delivery, etc. The software may include graphing capabilities and spreadsheets and other data displays. In certain embodiments, the second module is configured to display information from the software on the computer. For example, the second module may be configured to display a graph of medication delivery over a certain time, such as the basal delivery for the past twenty-four hours. In another embodiment, the first module may be controlled from a remote location, the remote location being a PC.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for infusing a fluid into a body from an external infusion device, comprising:
   activating one or more icons displayed on a second module of an external infusion device to select one or more program menus formed by the one or more icons, the external infusion device having a first module, the first module including a reservoir to hold fluid, a pump to pump the fluid from the reservoir, and an alarm, and the second module, the second module including a display and being removably attachable to the first module;
   programming pump flow commands to be communicated from the second module, wherein the first module dispenses the fluid through the pump in the first module in accordance with the pump flow commands received from the second module, and wherein the alarm is triggered when a user's blood glucose level value goes beyond an allowed value range; and
   removing the second module from the first module, wherein the first module continues fluid delivery when not attached to the second module.

2. The method of claim 1, wherein the second module removably attaches to the first module by sliding onto the first module.

3. The method of claim 1, wherein the second module removably attaches to the first module by snapping onto the first module.

4. The method of claim 1, wherein the second module removably attaches to the first module by hook and loop fasteners.

5. The method of claim 1, wherein the display is touch sensitive.

6. The method of claim 1, wherein the display further includes customizable settings.

7. The method of claim 1, further including using a Global Positioning System (GPS) device.

8. The method of claim 1, wherein the second module is compatible with a replacement of the first module.

9. The method of claim 1, wherein the first module is compatible with a replacement of the second module.

10. The method of claim 1, wherein the alarm is triggered when communication between the first module and the second module is disrupted.

11. A method for infusing a fluid into a body from an external infusion device, comprising:
activating one or more icons displayed on a second module of an external infusion device to select one or more program menus formed by the one or more icons, the external infusion device having a first module, the first module including a reservoir to hold fluid, a pump to pump the fluid from the reservoir, and an alarm, and the second module, the second module including a display and being removably attachable to the first module; and
programming pump flow commands to be communicated from the second module, wherein the first module dispenses the fluid through the pump in the first module in accordance with the pump flow commands received from the second module, and wherein the second module is easily attachable to and removable from the first module without interrupting fluid delivery from the first module.

12. The method of claim 11, further including storing the fluid delivery program in a memory.

13. The method of claim 12, further including retrieving the stored fluid delivery program from the memory to control fluid delivery.

14. The method of claim 11, wherein the alarm is triggered when there is a pump blockage.

15. The method of claim 11, wherein the alarm is triggered when a malfunction is detected.

16. The method of claim 11, wherein the second module removably attaches to the first module by sliding onto the first module.

17. The method of claim 11, wherein the second module removably attaches to the first module by snapping onto the first module.

18. The method of claim 11, wherein the second module removably attaches to the first module by hook and loop fasteners.

19. The method of claim 11, wherein the display is touch sensitive.

20. The method of claim 11, wherein the display further includes customizable settings.

21. The method of claim 11, further including using a Global Positioning System (GPS) device.

22. A method for infusing a fluid into a body from an external infusion device, comprising:
activating one or more icons displayed on a second module of an external infusion device to select one or more program menus formed by the one or more icons, the external infusion device having a first module, the first module including a reservoir to hold fluid, a pump to pump the fluid from the reservoir, and an alarm, and the second module, the second module including a display and being removably attachable to the first module;
programming pump flow commands to be communicated from the second module, wherein the first module dispenses the fluid through the pump in the first module in accordance with the pump flow commands received from the second module, and wherein the alarm is triggered when communication between the first module and the second module is disrupted; and
removing the second module from the first module, wherein the first module continues fluid delivery when not attached to the second module.

23. The method of claim 22, wherein the second module removably attaches to the first module by sliding onto the first module.

24. The method of claim 22, wherein the second module removably attaches to the first module by snapping onto the first module.

25. The method of claim 22, wherein the second module removably attaches to the first module by hook and loop fasteners.

26. The method of claim 22, wherein the display is touch sensitive.

27. The method of claim 22, wherein the display further includes customizable settings.

28. The method of claim 22, further including using a Global Positioning System (GPS) device.

29. The method of claim 22, wherein the second module is compatible with a replacement of the first module.

30. The method of claim 22, wherein the first module is compatible with a replacement of the second module.

* * * * *